United States Patent [19]

van der Maas

[11] 4,338,254
[45] Jul. 6, 1982

[54] PROCESS FOR THE PREPARATION OF COBALT (III) ACETYLACETONATE

[75] Inventor: Hendrikus J. H. van der Maas, Zuilichem, Netherlands

[73] Assignee: Chemische Fabriek Zaltbommel, Zaltbommel, Netherlands

[21] Appl. No.: 197,462

[22] Filed: Oct. 16, 1980

[30] Foreign Application Priority Data

Oct. 19, 1979 [NL] Netherlands ........................ 7907742

[51] Int. Cl.$^3$ .............................................. C07F 15/06
[52] U.S. Cl. ................................ 260/439 R; 260/429 J
[58] Field of Search ........................ 260/439 R, 429 J

[56] References Cited

U.S. PATENT DOCUMENTS 3,590,062  6/1971  Costa et al. ...................... 260/429 J
4,008,260  2/1977  Kunstle et al. ............... 260/429 J X Primary Examiner—Helen M. S. Sneed
Attorney, Agent, or Firm—Felfe & Lynch

[57] ABSTRACT

A process for the preparation of cobalt (III) acetylacetonate by oxidation of cobalt (II) acetylacetonate by means of hydrogen peroxide in the presence of the stoichiometrically required amount of acetylacetone in an organic solvent, wherein the organic solvent used is a solvent that is miscible with water and is inert to hydrogen peroxide, and in which the cobalt (II) acetylacetonate was prepared and is present in solution.

12 Claims, No Drawings

PROCESS FOR THE PREPARATION OF COBALT (III) ACETYLACETONATE

BACKGROUND OF THE INVENTION

1. Field of the Invention

This invention relates to a process for the preparation of cobalt (III) acetylacetonate wherein cobalt (II) acetylacetonate is reacted with hydrogen peroxide in the presence of acetylacetone to give cobalt (III) acetylacetonate. The reaction is carried out with a dissolved starting product prepared in a special manner.

2. Discussion of the Prior Art

It is known from German Auslegeschrift No. 24 20 691 (NOA 75 03 276) to react cobalt (II) acetylacetonate with hydrogen peroxide and acetylacetone to give cobalt (III) acetylacetonate. There a cobalt (II) acetylacetonate is used which has been prepared by reacting a cobalt (II) salt in an aqueous solution with acetylacetone by known procedures. A cobalt (II) acetylacetonate produced in this manner always contains two moles of water of crystallization, and these can only be eliminated by very costly means.

Moveover, in this prior-art process the oxidation is carried out in any desired organic solvent, the preferred solvents being aromatic hydrocarbons or alcohols. A drawback of this process is that a previously prepared cobalt(II) acetylacetonate must be used whose preparation is itself very costly. The reason for this is that in these known production processes the reaction product must be neutralized with ammonia, following which the ammonium salts must be carefully washed out.

Even though pure cobalt(II) acetylacetonate is used, in the process of German patent application DAS 24 20 691 the yields of anhydrous cobalt(III) acetylacetonate range only from 75 to 85%.

Thus there has been a need for preparing cobalt(III) acetylacetonate in such a way that yields of preferably over 95% are obtained. There has further been a need for developing a process for the preparation of cobalt-(III) acetylacetonate which does not require the use of isolated cobalt(II) acetylacetonate as a starting material.

SUMMARY OF THE INVENTION

To fill these needs, a process for the preparation of cobalt (III) acetylacetonate by oxidation of a cobalt (II) acetylacetonate in an organic solvent with hydrogen peroxide in the presence of acetylacetone has now been developed which is characterized in that the organic solvent used is an organic solvent which is miscible with water and is inert to hydrogen peroxide, and in which the cobalt (II) acetylacetonate has been produced and is present in solution. Preferably the solvent is inert to hydrogen peroxide at temperatures up to 120° C. but at least inert under the conditions of the reaction.

The process in accordance with the invention makes it possible to obtain the cobalt(III) acetylacetonate directly from a cobalt(II) compound without the need to isolate an intermediate product and to carry out a costly intermediate washing step. Yields of better than 95% are obtained, based on the cobalt(II) compound. The product is obtained is practically anhydrous and contains no cobalt(II) salt.

Of importance in the present process is the choice of solvent. The solvents recited verbatim in German patent application DAS No. 24 20 691 are not suited for use in the process of the invention since they are either not miscible with water or not inert to hydrogen peroxide at elevated temperatures.

The solvents which may be used in accordance with the invention include lower ketones such as acetone and methyl ethyl ketone. Also suited are dioxane, dioxolane and tetrahydrofuran. The preferred solvent is acetone.

The process of the invention is further characterized in that the cobalt(II) acetylacetonate used as starting product is not used in isolated form. This is made possible by preparing the cobalt(II) acetylacetonate in the solvent used for the reaction of the cobalt (II) acetylacetonate and hydrogen peroxide. It is prepared, in a manner which as such is known, by reacting a cobalt (II) compound with acetylacetone at elevated temperature. The cobalt compound used can be $Co(OH)_2$, CoO or basic cobalt (II) carbonate. The reaction temperature ranges from 20° to 100° C. and is preferably the boiling temperature of the solvent. The procedure employed may also be such that the evaporating solvent is condensed, with the condensate passing over a water-absorbing medium which also retains evaporated water, the rest of the condensate being recycled to the reaction vessel. In this way it is possible to monitor the progress of the reaction and to recognize the end of the reaction, which results in the formation of the cobalt (II) acetylacetonate.

The amount of acetylacetone added to the reaction mixture along with the cobalt(II) compound is at least equal to the amount stoichiometrically required for preparation of the cobalt(II) acetylacetonate. However, the amount of acetylacetone stoichiometrically required for formation of the desired cobalt(II) acetylacetonate may also be used from the very start of the overall reaction.

With the procedure carried out in the solvent in accordance with the invention, a cobalt(II) acetylacetonate that is free of water of crystallization is formed as an intermediate product. The latter is in solution in the solvent and without being isolated is oxidized in that solution with $H_2O_2$ to cobalt (III) acetylacetonate, in a manner which as such is known. The oxidation is effected in the presence of the stoichiometrically required amount of acetylacetone.

This reaction is carried out a temperatures ranging from 40° to 100° C., and preferably from 50° to 90° C. It is best carried out at the boiling temperature of the solvent. The process is conveniently carried out at atmospheric pressure.

The hydrogen peroxide is preferably added in a 25 to 35% aqueous solution. Complete oxidation can be secured with even a slight excess of up to 10 weight percent. As a rule, however, a molar excess of from 1.1 to 1.5 will be used.

It is advisable to add the hydrogen peroxide in portions so that it can always be eliminated by reaction immediately after having been added. The addition of hydrogen peroxide is terminated when there is no longer any cobalt(II) salt present. This is readily determined by subjecting a sample to thin-layer chromatography.

When all of the cobalt(II) salt has been oxidized to cobalt(III) salt, the temperature is reduced to between 25° and 10° C.. The cobalt(III) acetylacetonate is then obtained as an anhydrous salt. It can readily be dried at temperatures of up to 90° C. Drying will be facilitated if it is done in a vacuum. A vacuum down to 30 millibars will be perfectly adequate.

After separation of the cobalt (III) acetylacetonate crystals, the mother liquor of a batch can readily be used with a new batch. Byproducts which might interfere with the reaction will not be present in any significant amount.

Cobalt (III) acetylacetonate is useful as for polymerisation and vulcanization reactions, for coloring of synthetic resins and as intemediate for synthesis.

In order to more fully illustrate the nature of the invention and the manner of practicing the same, the following examples are presented.

EXAMPLE 1

93 g cobalt hydroxide was suspended in 300 ml acetone in a reaction vessel equipped with reflux condenser and distillation bridge. 315 g acetylacetone was then added with stirring, which resulted in a slight temperature rise.

The mixture was heated to reflux. The acetone distilled off was conducted over calcium chloride for absorption of the entrained water. After 2 hours' heating to boiling temperature, an appreciable amount of water had been bound to the calcium chloride.

Over a period of from 3 to 3½ hours, 100 g hydrogen peroxide was then added as a 35% aqueous solution through a dropper funnel while the reaction mixture was held at reflux temperature, the distillation bridge having been removed. The internal temperature ranged from 60° to 65° C.

After a total of 100 g hydrogen peroxide solution had been added, a sample was subjected to thin-layer chromatography, which showed that there was no longer any cobalt(II) salt present. The reaction mixture was then cooled to 10° C. The green-black crystals which precipitated were separated by filtration and washed with 75 ml acetone. It proved possible to dry the product in air to a moisture content of not more than 0.2%. In this way, 338.7 g cobalt(III) acetylacetonate was obtained. (Yield: 95.1%, based on the cobalt hydroxide used.) Analysis showed that the metal content was between 16.54 and 16.59%. The theoretical value is 16.57%.

EXAMPLE 2

93 g cobalt hydroxide was suspended in the mother liquor and wash acetone from Example 1, and 315 g acetylacetone was then added to it. The mixture was heated to reflux temperature with stirring, and the acetone so distilled off was dried over calcium chloride as in Example 1.

After a reaction time of 2 hours, the dropwise addition of a 35% hydrogen peroxide solution was started. The internal temperature rose from 60° to 65° C. A total of 95 g hydrogen peroxide was added over a period of 3 hours.

A sample subjected to thin-layer chromatography at the end of that time showed that there was no longer any cobalt(II) salt present. The temperature then was again reduced to 10° C., whereupon large, green-black crystals precipitated. These were separated by filtration and washed with 80 ml acetone.

The washed crystals were then dried in a vacuum of 40 millibars for 1 hour at 80° C., 344 g cobalt(III) acetylacetonate was obtained, corresponding to a yield of 96.6%. The metal content ranged from 16.48 to 16.56%, and the water content was not more than 0.1%.

EXAMPLE 3

This example shows that the preparation of cobalt(II) acetylacetone may be effected also without absorption of the water formed.

128 g basic cobalt carbonate was suspended in 300 ml acetone. 210 g acetylacetone was then added at room temperature. This initiated the reaction, which manifests itself by the evolution of gas and a color change. The mixture was heated to reflux temperature, and 105 g acetylacetone was then added and the reflux temperature maintained for another hour.

The dropwise addition of a 35% hydrogen peroxide solution through a dropper funnel was then started. In this way, 100 g hydrogen peroxide was added over a period of 4½ hours. A sample subjected to thin-layer chromatography at the end of that time showed that there was no longer any cobalt(II) salt present.

After the reaction mixture had been cooled to 10° C., the crystals so obtained were separated by filtration and washed with 75 ml acetone. The solid obtained was dried in a vacuum of 40 millibars for 1 hour at 80° C. 343 g was obtained, which corresponds to 96.4% of theory. Analysis showed that the metal content ranged from 16.51 to 16.58%. The water content was not more than 0.2%.

EXAMPLE 4

After drying over calcium chloride, 90 ml acetone was added to the mother liquor and wash acetone from Example 3. 128 g basic cobalt carbonate was then suspended in that solution. 215 g acetylacetone was then added with stirring. The reaction manifested itself at once by a change in the color and shape of the crystals. Also there was evolution of gas, and the mixture became considerably more difficult to stir.

The mixture was then heated to reflux temperature, and another 105 g acetylacetone was added. Boiling was continued for about another half hour with reflux, the acetone distilled off being conducted over calcium chloride. The dropwise addition of a 35% hydrogen peroxide solution was then begun.

By the end of 4½ hours, 92 g hydrogen peroxide had been added, and the test for cobalt(II) salt was negative. The reaction mixture was then cooled to 10° C. Green-black crystals were so obtained, which were then separated by filtration and washed with 75 ml acetone, after which they were dried at room temperature.

346 g cobalt(III) acetylacetonate was obtained, which represents 97.2% of theory. Analysis showed that the cobalt content was between 16.55 and 16.56%. The water content was less than 0.2%.

EXAMPLE 5

128 g basic cobalt carbonate was stirred into 400 ml acetone. The mixture was heated to reflux. The internal temperature was 66° C. 315 g acetylacetone was then added. A 35% solution of hydrogen peroxide was then added dropwise over a period of 4 hours. By the end of that time, a total of 100 g hydrogen peroxide had been added. The reaction was then allowed to proceed for another half hour. Then the reaction mixture was cooled to 15° C. and the crystals obtained were separated by filtration and washed with 100 ml acetone, which was followed by drying in a vacuum of 45 millibars at 90° C. 336 g (94.4%) cobalt(III) acetylacetonate with a water content of not more than 0.2% and a metal content ranging from 16.54 to 16.59% was obtained.

From the remaining mother liquor, 410 ml acetone with a water content of 11.8% was distilled off. Upon evaporation of this mother liquor, more cobalt(III) acetylacetonate precipitated. This was filtered off and dried as described above. In this way, another 11 g cobalt(III) acetylacetonate was obtained, so that the total yield was 347 g, or 97.5%, based on the cobalt carbonate used.

What is claimed is:

1. In a process for the preparation of cobalt (III) acetylacetonate by oxidation of cobalt (II) acetylacetonate by contacting the same with hydrogen peroxide in the presence of a the stoichiometrically required amount of acetylacetone in an organic solvent, the improvement wherein the organic solvent used is a solvent that is miscible with water and is inert to hydrogen peroxide, and in which the cobalt (II) acetylacetonate was prepared and is present in solution and carrying out the process at a temperature between 40° and 110° C.

2. A process for the preparation of cobalt (III) acetylacetonate according to claim 1, wherein the solvent used is acetone.

3. A process for the preparation of cobalt (III) acetylacetonate according to claim 1, wherein the preparation of the cobalt (II) acetylacetonate is effected with such excess of acetylacetone as is necessary for preparation of the cobalt (III) acetylacetonate.

4. A process according to claim 1, wherein the reaction of the cobalt (II) compound with acetylacetone is carried out at the boiling temperature of the solvent with reflux.

5. A process according to claim 4, wherein the solvent is conducted over an absorbent for water.

6. A process according to claim 1, wherein the hydrogen peroxide is in the form of a 25 to 35 percent by weight aqueous solution.

7. A process according to claim 1, wherein the solvent is selected from the group consisting of acetone, methyl ethyl ketone, dioxane, dioxolane and tetrahydrofuran.

8. A process according to claim 1, wherein the solvent is a ketone of the formula

wherein $R_1$ and $R_2$ are independently alkyl or cycloalkyl of up to 6 carbon atoms 9. A process for the preparation of cobalt (III) acetylacetonate which comprises:

(A) contacting a cobalt (II) compound with acetylacetone at elevated temperature in the presence of an organic solvent, which is miscible with water and is inert to hydrogen peroxide, whereby to obtain cobalt (II) acetylacetonate; and (B) contacting said cobalt (II) acetylacetonate while dissolved in said solvent with hydrogen peroxide in the presence of the stoichiometrically required amount of acetylacetone.

10. A process for preparing cobalt (II) acetylacetonate which comprises contacting a cobalt (II) compound with an at least stoichiometric amount of acetylacetone in an organic solvent which is miscible with water and inert to hydrogen peroxide.

11. A process according to claim 10, wherein the process is carried out at a temperature from 20° to 100° C.

12. A process according to claim 11, wherein said cobalt (II) compound is cobalt dihydroxide, cobalt oxide, or basic cobalt (II) carbonate.

* * * * *